United States Patent [19]

Glajch et al.

[11] Patent Number: 5,147,631
[45] Date of Patent: Sep. 15, 1992

[54] POROUS INORGANIC ULTRASOUND CONTRAST AGENTS

[75] Inventors: Joseph L. Glajch, Nashua, N.H.; Gary L. Loomis, Drexel Hill, Pa.; Walter Mahler, Wilmington, Del.

[73] Assignee: Du Pont Merck Pharmaceutical Company, Wilmington, Del.

[21] Appl. No.: 693,476

[22] Filed: Apr. 30, 1991

[51] Int. Cl.$^5$ .......................... A61K 49/00; A61B 8/00
[52] U.S. Cl. ..................................... 424/9; 128/662.02
[58] Field of Search ...................... 128/660.01, 662.02; 424/4, 9

[56] References Cited

U.S. PATENT DOCUMENTS

| | | | |
|---|---|---|---|
| 4,844,882 | 7/1989 | Widder et al. | 424/9 |
| 4,900,540 | 2/1990 | Ryan et al. | 128/662.02 |
| 4,957,656 | 9/1990 | Cerny et al. | 128/662.02 |

*Primary Examiner*—Francis Jaworski
*Attorney, Agent, or Firm*—Blair Q. Ferguson

[57] ABSTRACT

The invention relates to ultrasound contrast agents comprising porous particles of an inorganic material containing an entrapped gas or liquid and having an average particle diameter of about 0.05 to 500 microns, said inorganic material being selected from one or more of the group consisting of: monomeric or polymeric borates; monomeric or polymeric aluminas; monomeric or polymeric carbonates; monomeric or polymeric silicas; and monomeric or polymeric phosphates; and pharmaceutically acceptable organic or inorganic cationic salts thereof.

60 Claims, 1 Drawing Sheet

POROUS INORGANIC ULTRASOUND CONTRAST AGENTS

BACKGROUND OF THE INVENTION

Techniques for ultrasound imaging various parts of the body are well known. An ultrasonic scanner is placed on the body surface overlying the area to be imaged. The sound waves generated by the scanner are directed toward the area to be imaged. The scanner then detects sound waves reflected from the underlying area and translates the signal into images.

The acoustic properties of a substance, such as an organ system, will depend upon the velocity of the ultrasonic transmissions and the density of the substance. Changes in the substance's acoustic properties will be most prominent at the interface of components of the substance differing in density, such as solid, liquid, and gas components. When ultrasonic energy is transmitted through a substance, the changes in acoustic properties (e.g., density) of the substance cause changes in the reflection characteristics, resulting in a more intense sound reflection signal received by the ultrasonic scanner.

Ultrasound contrast agents are introduced into the body organ system being imaged using ultrasound, and there act to influence the ultrasound signal in a way that enhances the ultrasound image. The contrast agent may be ingested or injected into and perfuse the microvasculature of the tissue desired to be imaged, to provide clearer images of the tissue. Such ultrasound contrast agents may be useful in helping to diagnose diseases earlier and more accurately.

Liquid and solid contrast agents containing entrapped gas are known in the art. The microbubbles provided by these contrast agents act as sound wave reflectors because of the acoustic differences between the gas microbubble and surrounding liquid.

Feinstein, U.S. Pat. No. 4,572,203, issued Feb. 25, 1986 discloses "microbubbles" of about 6-20 microns diameter produced by sonication of certain viscous solutions, as ultrasound contrast agents. Feinstein, U.S. Pat. No. 4,572,203, issued Feb. 25, 1986 also discloses solid or semi-solid metal-containing microparticles, such as glass or graphite, not containing trapped air, small enough to pass through capillaries, as ultrasound contrast agents. Also disclosed are microspheres formed from an amino acid polymer matrix, such as albumin, with magnetic particles, such as magnetite ($Fe_3O_4$) embedded therein.

Tickner, U.S. Pat. No. 4,265,251, issued May 5, 1981 discloses the use of certain saccharide composition "microbubble" particles with a hollow gas-filled interior space as ultrasound enhancing agents.

Rasor and Tickner, U.S. Pat. No. 4,442,843, issued Apr. 17, 1984, U.S. Pat. No. 4,657,756, issued Apr. 14, 1987, and U.S. Pat. No. 4,681,119, issued Jul. 21, 1987, to Schering, disclose aggregates of microparticles (of 1-50 micron diameter) of a solid material, which are soluble in blood, containing gas in the voids between the particles, or with gas adsorbed on the surface of the particle, or containing gas as an integral part of the internal structure of the particle, for use in ultrasound imaging. The following solid materials are disclosed: various saccharides, NaCl, sodium citrate, sodium acetate, sodium tartrate, $CaCl_2$ and $AlCl_3$.

Hilmann et al., European Patent Application Publication Number 122,624, to Schering, published Oct. 24, 1984 discloses microparticles comprised of a solid surface-active substance, including various organic lipophilic compounds, with enclosed air, as ultrasound contrast agents. Also dislosed is the combination of particles of the surface-active material and particles of a non-surface active material, such as sodium chloride, sodium citrate, sodium acetate, sodium tartrate, and various saccharides.

SUMMARY OF THE INVENTION

This invention relates to ultrasound contrast agents comprising porous particles of an inorganic material having an average particle diameter of about 0.05 to 500 microns and containing entrapped gas or liquid. The inorganic material includes monomeric and polymeric forms, and mixtures of monomeric and polymeric forms of one or more of the following: borates; aluminas; carbonates; silicates; silicas; aluminosilicates; and phosphates; and organic or inorganic cationic salts thereof. The inorganic material may be in a crystalline and amorphous form, or a mixture of crystalline and amorphous forms.

Representative inorganic materials useful in the present invention include $SiO_2$, alkali salts of $CO_3^{-2}$ and $HCO_3^{-1}$, alkali salts of $HPO_4^{-2}$, aluminum oxides and hydroxides, such as $Al_2O_3$, alkali salts of aluminosilicates, and $H_3BO_3$.

The inorganic particles can be prepared and fabricated using known techniques into a variety of shapes, sizes, and extents of porosity. The particles contain one or more pores or cavities, which may be entirely or partially enclosed by the inorganic material particle shell. For parenteral use, the particles are preferably about 0.2-10 microns in average diameter.

The porous particles of the invention contain an entrapped gas or liquid to provide a suitable echogenic interface to enhance an ultrasound image.

The porous gas-containing inorganic particles of the invention should have a density that is less than about 90% of the density of the solid nonporous inorganic material, and preferably have a density that is less than 60% of the density of the solid nonporous inorganic material. The pore diameter may vary depending on the size of the particle and the number of pores, to achieve the preferred particle density. Thus, the pore size may range from about 20 angstrom to 500 microns.

The porous inorganic particles of the invention may be coated with a variety of organic polymeric and lipid materials to control the stability, pharmacokinetics, targeting, and biological effects of the particles in vivo.

The porous inorganic particles of the invention are administered parentally or nonparentally with a pharmaceutically acceptable carrier to a person, to thereby enhance the ultrasound image of a tissue or organ system of that person.

DETAILED DESCRIPTION OF THE INVENTION

Figure 1:
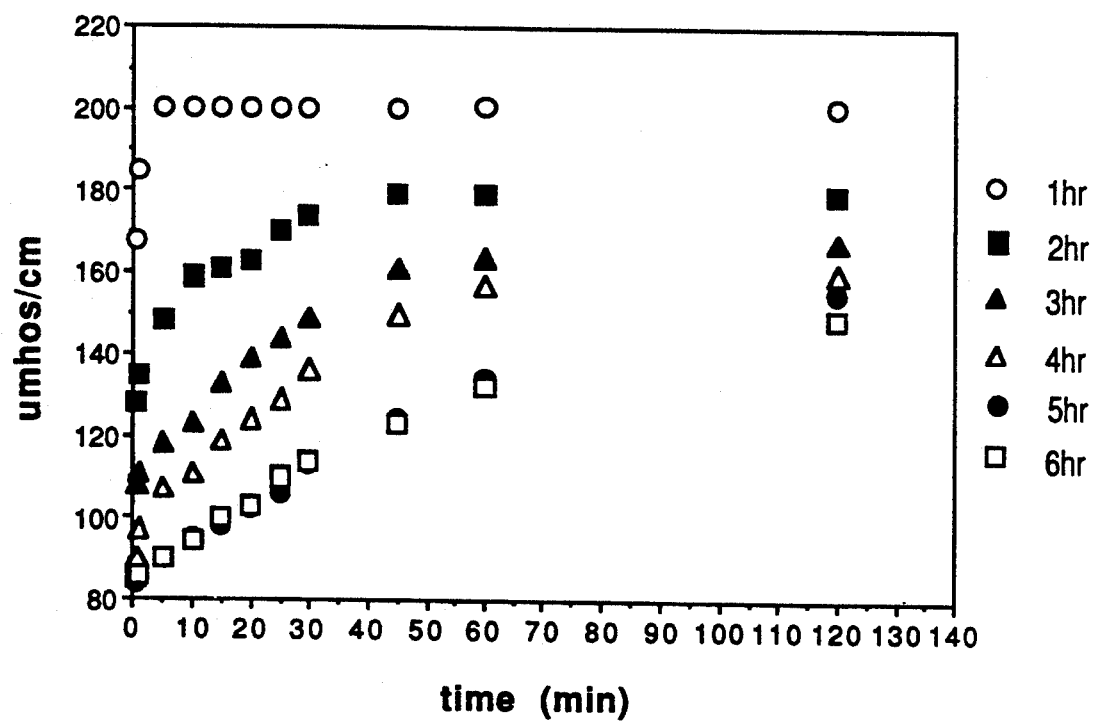
FIG. 1 shows the dissolution of solid phosphate particles as measured by solution conductivity ($\mu$mhos/cm) as a function of time following addition of the solid particles to water, as described under Example 2.

This invention relates to ultrasound contrast agents comprising inorganic porous particles useful for ultrasound imaging of a body organ system. Such contrast agents may be an important adjunct in ultrasound diagnostic procedures, for example, for cardiovascular and gastrointestinal uses. The inorganic porous particles of the invention provide contrast for ultrasound imaging; i.e., the particles act to reflect ultrasound waves and thereby enhance the ultrasound signal when introduced into the organ system being imaged using ultrasound.

Ultrasonic images can be used for quantitative diagnostic purposes, for determining blood flow, and the like, as described, for example, in U.S. Pat. Nos. 3,640,271, 4,265,251, and 4,276,885.

The inorganic material useful in the present invention may exist in an amorphous or glass state or in a crystalline state or in a mixture of amorphous and crystalline forms. The inorganic material useful in this invention includes borates, aluminas, carbonates, bicarbonates, silicas, silicates, aluminosilicates, and phosphates in the form of monomeric salts or as polymeric or condensed forms, or as mixtures of monomeric and polymeric forms. Particles comprising mixtures of these materials are also expected to be useful in the present invention. Inorganic materials useful in the present invention include, but are not limited to, $SiO_2$, alkali salts of $CO_3^{-2}$ and $HCO_3^{-1}$, alkali salts of $HPO_4^{-2}$, aluminum oxides and hydroxides, such as $Al_2O_3$, alkali salts of aluminosilicates, and $H_3BO_3$.

Phosphates, as the term is used herein, include various monomeric and condensed or polymeric crystalline forms and various noncrystalline or amorphous forms (including glass forms), as outlined below in Scheme I (adapted from Kirk and Othmer, Encyclopedia of Chemical Technology) and as described in Van Wazer (1958) Phosphorus and Its Compounds, Volume 1, pp 419-770, Interscience Publishers, New York, a standard textbook in the field of phosphate chemistry.

As shown in Scheme I, the condensed or polymeric phosphates are prepared by dehydration of orthophosphates under various conditions of increased temperature for example:

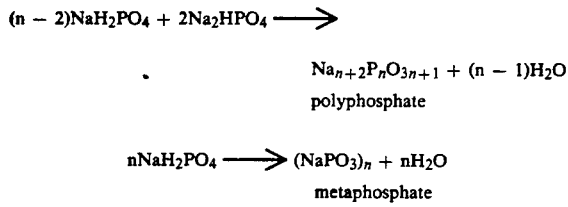

$$(n - 2)NaH_2PO_4 + 2Na_2HPO_4 \longrightarrow$$

$$Na_{n+2}P_nO_{3n+1} + (n - 1)H_2O$$
polyphosphate $$nNaH_2PO_4 \longrightarrow (NaPO_3)_n + nH_2O$$
metaphosphate Scheme I

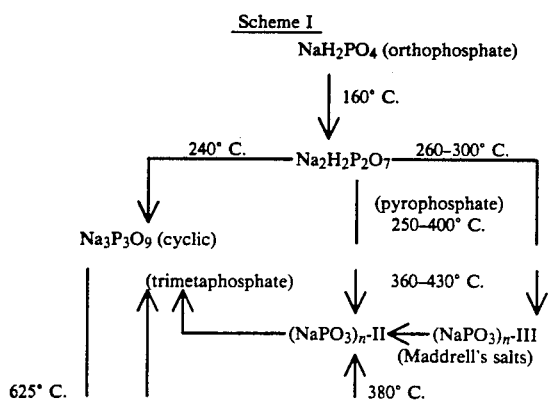

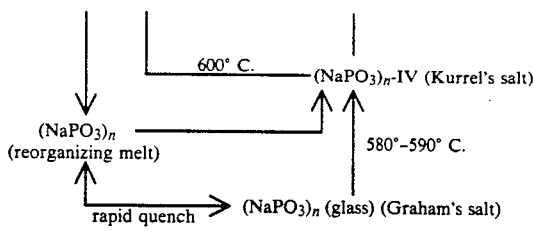

In Scheme I, sodium phosphate is shown; analogous forms of phosphate exist for other salts of phosphate, such as the alkali earth cations.

The preparation of various monomeric and condensed or polymeric forms of phosphate, as shown in Scheme I, is appreciated by those skilled in the art of phosphate chemistry and is described in standard treatises on phosphate chemistry, for example, Van Wazer (1958) Phosphorus and Its Compounds, Volume 1, pp 419-770, Interscience Publishers, New York.

The term phosphates, as used herein, also includes derivatives of phosphates containing additional elements. For example, nitrogen can be incorporated into phosphate glasses to form oxynitride glasses, as described by Reidmeyer et al. (1986) J. Non-crystalline Solids 85: 186-203, the teaching of which is incorporated herein by reference. Nitriding the phosphate starting glass is expected to decrease the dissolution rate of the solid in water and increase the chemical stability of the solid. The preparation of phosphorus oxynitride glass by melting sodium metaphosphate in anhydrous ammonia to produce glasses containing up to 12 wt % nitrogen is described by Reidmeyer et al. Porous particles of oxynitride glasses and crystalline solids useful in the present invention can be prepared using the methods, described below.

Silicates and silicas, as used herein, includes any and all siliceous materials in the particulate form stated above. Typical silica material includes $SiO_2$, silicate-containing minerals, and synthetic silicates such as silica gels, powders, porous glass and those prepared by hydrolysis of calcium silicide or sodium silicate. The preparation of porous silica particles is described in Bergna and Kirkland, U.S. Pat. No. 4,131,542, Kirkland, U.S. Pat. No. 3,782,075, and Kirkland, U.S. Pat. No. 3,505,785, the teaching of which is incorporated herein by reference.

The inorganic particles of the invention have the advantages of good mechanical stability and rigidity, which are important attributes lacking in other materials used as ultrasound contrast agents, such as sonicated albumin microspheres and perflurorocarbon emulsions. In addition, inorganic particles can be prepared and fabricated, using known techniques, into a variety of shapes, sizes, and extents of porosity, in order to obtain the most desirable contrast effects. In addition, inorganic porous particles can be prepared with a range of different solubilities in aqueous solution, such as a body fluid. The solubility of the inorganic porous particle may affect the rate of biodegradation and clearance of the agent in vivo and may, thereby, be an important property affecting the biological responses and toxicity associated with the ultrasound contrast agent.

The inorganic porous particles useful in the present invention comprise an inorganic solid material that encloses or partially encloses one or more pores or cavities. The porous particles of the invention contain an entrapped gas or liquid to provide a suitable echogenic interface to enhance an ultrasound image. The pore or pores may be completely enclosed or encapsulated by the inorganic material or may be partially enclosed and open to the surface of the particle. Thus, the particles are porous or hollow and contain an entrapped or partially entrapped gas or liquid in the pore or pores. Porous inorganic particles useful in this invention include particles having a single pore enclosed by a solid shell; i.e., hollow particles. Alternatively, the porous particle may have a single pore which is partially enclosed by a solid shell. The porous particles of the invention also include particles containing a plurality of pores. The pores may be interconnected and may connect to an opening at the surface of the particle. The particles may also contain pores which are completely enclosed and are not interconnected or open to the surface of the particle. Particles with non-interconnected and completely enclosed pores are known as closed cell foam type particles.

The inorganic particles useful in the present invention may range in size and shape or morphology. A variety of particle shapes are useful in the present invention. For example, the particles may range from roughly spherical shapes to rod-like shapes and may be regular or irregular in shape. The particle size, measured as the average particle diameter, should be in the range of about 0.01 microns to 1 millimeter. For irregular shaped particles, the term average particle diameter refers to the effective particle diameter or Stokes diameter of the particle. For injection or parenteral administration, the particles are preferably about 0.2–10 microns in diameter. For non-parenteral administration, such as ingestion, larger particles may be acceptable or preferred.

For purposes of tissue perfusion, the porous inorganic particle should preferably be about 0.2–10 microns in diameter and thereby small enough to pass through capillaries, which are about 8 to 10 microns in diameter, so as to perfuse the tissue. The porous inorganic particles of the invention should be small enough to permit their passage through capillaries without being filtered out and capable of perfusing the tissue and produce an enhanced ultrasound image that is of resolution sufficient to distinguish, for example, between well perfused and poorly perfused tissue for the detection and diagnosis of ischemia.

The porous gas-containing inorganic particles of the invention should have a density that is less than about 90% of the density of the solid nonporous inorganic material, and preferably are less than 60% of the density of the solid nonporous inorganic material. The density of the gas-containing porous inorganic particles of the invention is preferably about 0.2–50% of the density of the non-porous inorganic material. The pore diameter may vary depending on the size of the particle and the number of pores, to achieve the preferred particle density. Thus, the pore size may range from about 20 angstrom to 500 microns. The pore diameters may be in the range of about 20 to 2000 angstrom for porous particles having a plurality of pores. For porous particles having a single pore, the thickness of the solid shell may vary. The shell thickness may be about 1–45% of the diameter of the particle. Thus, for porous particles having a single pore (i.e., hollow particles) ranging in particle size from about 0.2 to 500 microns, the pore size may correspondingly vary from about 0.2 to 500 microns.

The porous inorganic particles typically have a specific surface area of about 1 to 1500 $m^2/g$. The porous inorganic particles of the invention may have a gas volume per gram of particle of greater than 0.05 mL/g, and preferably in the range of about 0.05 to 50 mL/g.

Porous inorganic particles of the invention, useful as ultrasound contrast agents, may be prepared using standard methods for the preparation of porous particles. For example, porous inorganic particles may be prepared using standard methods involving the spraying of a metal salt solution into a furnace at elevated temperatures, such as standard spray drying, evaporation decomposition, high temperature aerosol decomposition, or drop-generator procedures (see below).

The spray-drying procedure, as applied for the preparation of porous silica particles is described in Bergna and Kirkland, U.S. Pat. No. 4,131,542, the teaching of which is incorporated herein by reference. Similar procedures can be used for the preparation of porous particles composed of other materials including borates, aluminates, carbonates, phosphates, and mixtures thereof.

The drop-generator process for preparing high precision glass spheres is described by Hedricks (1984) Glass Science and Technology, volume 2, pp 149–168, (ed. Uhlmann and Kreidl) Academic Press, the teaching of which is incorporated herein by reference.

The high temperature aerosol decomposition (HTAD) process is described by Moser and Lennhoff (1989) Chem. Eng. Comm. 83: 241–259, the teaching of which is incorporated herein by reference. This procedure involves the spraying of a metal salt solution into a tube furnace at elevated termperatures, resulting in solvent evaporation, salt decomposition, and metal oxide ceramic particle formation. The HTAD of Moser and Lennhoff may be used for the synthesis of metal oxide particles having a range of surface areas and a range of particle morphologies, from nearly perfect hollow spheres to fragmented particles. By controlling the HTAD reactor conditions, materials having the desired morphology (spheres or fragmented particles), high or low surface area, phase purity, compositional purity, pore size distribution, and aqueous solubility may be obtained.

Hollow inorganic particles (i.e., particles having a single pore) may also be prepared by the process of coating a template or core particle composed of a material, such as polystyrene latex, with the inorganic material to form a shell around the core particle, and then subsequently removing the template or core material. Removal of the core can be achieved, for example, by heating and calcination of the core material. In such a process, the inorganic particle size, pore size, and thickness of the inorganic shell can be controlled quite precisely. Such a process of preparing hollow spherical particles is described by Kawahashi and Matijevic (1990) J. of Colloid and Interface Science 143:103–110.

The gas in the pore or pores of the porous inorganic particle may be a pure gas or mixture of gases, such as air. For example, elemental gases such as $O_2$, $N_2$, $H_2$, He, argon, and other noble gases, and other light gases, such as $CO_2$, $CF_4$, or $C_2F_6$ are expected to provide useful ultrasound contrast properties. The gases may be incorporated into the pores of the particles, for example, by exchange at high temperature and/or high pressure.

The porous inorganic particles useful in the present invention may have a range of solubility in aqueous solution. Porous inorganic particles of any desired solubility can be obtained in several ways. The solubility can be controlled by selection of the desired particle surface area, the particle shell thickness, and/or the type of solid used in the particle. The inorganic particles may be comprised of a relatively insoluble solid, such as silicate materials, or may be relatively soluble in aqueous solution. For example, as discussed below, the solubility of phosphate materials can be controlled by the temperature and heating time used to prepare various amorphous or crystalline forms of phosphate material.

The porous inorganic particles must have a sufficiently slow dissolution rate in aqueous solution so as to exist in vivo following administration for at least about 1-30 minutes to provide enough time for the imaging procedure to be performed. For certain imaging applications, such as cardiovascular applications, where the contrast agent is administered parenterally, it may be desirable to use particles which are relatively soluble in serum or other body fluid. Porous inorganic particles having slower dissolution rates (reduced solubility) or insoluble particles, such as silica or alumina particles, may be desired for other uses, such as gastrointestinal imaging applications.

The porous inorganic particles of the present invention are administered with an acceptable carrier to a person to enhance the contrast and resolution of ultrasound imaging of the tissue or organ system that is being imaged. Thus, the inorganic particles must have acceptable biocompatibility and toxicity properties in humans. The biocompatibility criteria will depend in part on the type of ultrasound imaging application and route of administration of the ultrasound contrast agent. For example, the biocompatibility criteria may be different for gastrointestinal administration than for parenteral administration of the contrast agent.

Physiologically acceptable pharmaceutical carrier fluids are used to transport and preferably stabilize the suspension of the particles (prevent sedimentation), and retard the dissolution of the particles. Useful carrier fluids include, but are not limited to: water; aqueous solutions of one or more physiologically acceptable inorganic salts, such as physiological buffered solutions; aqueous solutions of mono- or disaccharides, such as galactose and lactose; and physiologically acceptable monofunctional or polyfunctional alcohols or their aqueous solutions. Also included are carrier fluids which enhance the adherence of the contrast agent to the organ or tissue walls or surface. Suitable pharmaceutical carriers are described in *Remington's Pharmaceutical Sciences*, Mack Publishing Co., a standard reference text in this field.

The porous inorganic particles of the invention optionally may be coated with an organic material, such as those materials described below, to control the stability, pharmacokinetics, targeting, and biological effects of the particles in vivo. Coating or microencapsulation of the particles can be used to enhance their stability in the formulation, to prevent aggregation, to alter their tissue distribution in the body and their elimination from the body, to reduce toxicity or enhance effectiveness, to reduce the adherence of biological materials which trigger immune reactions or thromboembolic reactions, to control the dissolution rate of soluble particles, and to control the permeation of water and other substances into and out of the particle matrix, among other uses.

Methods for coating solid particles are described by J. Bakan in The Theory and Practice of Industrial Pharmacy (L. Lachman, H. A. Lieberman, and J. L. Kanig, eds.) pp 419-429. The methods generally most useful for coating particles less than 100 micron approximate size include air suspension, coacervation-phase separation, multiorifice centrifugal, and solvent evaporation. The coating might vary in composition, thickness, and porosity, depending on the intended effect.

Representative organic materials to form the coating include organic polymeric substances including cellulose polymers such as ethylcellulose, hydroxypropylcellulose, methylcellulose, and hydroxypropylmethylcellulose, polyvinylpyrrolidone, polyethylene glycol, albumin, gelatin, starch, collagen, dextran and modified dextrans, polylactide/polyglycolide, polyalkylcyanoacrylates, polyacrylamide, lipids such as cholesterol, phosphatidylcholine, and phosphatidylinositol, and surfactants such as polysorbates, polyethylene ethers and esters, and polyoxyethylene/polyoxypropylene block polymers. The inorganic particles of the invention may also optionally be coated with a surface-active substance, such as those described by Hilman et al., European Patent Application Publication Number 122,624.

EXAMPLE 1

MEASUREMENT OF ULTRASOUND BACKSCATTER

A representative system and methods for measuring and comparing the acoustic energy backscattered from suspended materials under consideration as ultrasound contrast agents is desribed below. The acoustic energy backscatter properties of a material is indicative of the utility of that material as an ultrasound contrast agent. The system for measurement of ultrasound backscatter involves sample dilution, sample manipulation components, ultrasound generation and analog signal processing components, and data acquisition, storage and analysis.

Samples to be tested are introduced into a cell consisting of a cylindrical plastic tube with opposing 3-cm diameter acoustic windows of a 76 micrometer thick acetate polymer film. The lower 7-8 cm of the cell is immersed in a tank filled with distilled water. An immersible magnetic stirrer is positioned under the cell and a modified stirring bar maintains constant mixing of the sample fluid.

A 5 MHz unfocussed ultrasound transducer (Panametrics V309) is positioned horizontally in the water tank using a two-dimensional stepper-motor driven positioning fixture with 1 micrometer accuracy in the short dimension (across the test cell) and 10 micrometer accuracy in the long dimension (toward and away from the cell). The transducer is excited by a 300 volt pulser (part of Panametrics 5052UA). The signal from the transducer is directed (via a BNC T-adapter at the pulser output) to a battery-powered preamplifier (Panametrics 5670), then to a computer-controlled 120 dB switchable attenuator (HP 8494 and 8496G with HP11713 GPIB controllor). From here the signal is routed to a Metrotek MR106 receiver which includes a switchable detector, high-pass filter and 60 dB amplifier. The signal output then goes to one channel of a Tektronix 2440 digital storage oscilloscope which is interfaced via the GPIB controllor to a Macintosh II personal computer running LabView (National Instruments). Timing is maintained throughout using an external function generator as a master oscillator.

An acquisition routine sets the attenuator and takes data from a laboratory balance and from the oscilloscope, storing it in an ASCII encoded, TAB-delimited format text file. Data is stored with each waveform appended, row by row, to the end of the file and preceded by identification information; at the end of the study, the numeric data is read back in, transposed into column format and recombined with the identification information to form a second file. The analysis routine allows the operator to select a relevant portion of the A-line data within which to average and strips out the study identification information at the beginning of the file and the abcissa and correction information at the beginning of each column of data. This is used to correct for the attenuator setting and to calibrate both the concentration and power (or voltage) scales. Residual mass values for stock material introduced into the test cell (as well as cumulative values for fluid mass removed from the cell) are converted into particle and mass concentration scales and voltages are converted into dB equivalent gain. These are written, along with the data used for correction, to a third (output) file. Plots of dB equivalent voltage gain versus either particle concentration or mass concentration may then be obtained using a commercial software package such as KaleidaGraph TM (Synergy Software, Inc.).

A stock suspension is prepared and its concentration is either entered (for initially liquid samples) or is calculated by the program. The test cell is first filled with approximately 75 mL of reference material (for example, a suspension of Polysciences #19823 hollow glass spheres may be used), and a measurement taken. The reference material is returned to its container, and the cell washed thoroughly and filled with approximately 75 ml of distilled water. Another measurement is then taken and a small volume of the fluid is removed and recorded, a similar volume of the stock solution is added, and the residual mass of the stock syringe recorded. This step is repeated until the stock syringe is empty; the program is then allowed to transpose the data to create the file to be analyzed. For these measurements, the (1 cm diameter) transducer is positioned 6 cm from the near window of the cell, ensuring that all measurements are taken in the transducers far field region. It is centered visually in both the vertical and horizontal aspects. A measurement, as used above, consists of an average of at least 256 waveforms of the detected RF ultrasound signal. For each, the attenuation is adjusted to prevent nonlinear response and to maintain a signal at the oscilloscope which is large enough to avoid sampling error and significant noise contribution. Averaging is perfomed by the oscilloscope prior to transfer of data to the computer. Each component of the system was carefully evaluated using 3 Mhz, 5 Mhz and 7 Mhz sine wave signals for linearity and gain. Appropriate ranges for each were determined to ensure that no component of the system was being operated in a region in which the output was nonlinearly related to the input.

EXAMPLE 2

PREPARATION OF SOLID PHOSPHATE PARTICLES OF VARYING SOLUBILITY

An aqueous solution of disodium dihydrogen pyrophosphate was prepared by dissolving 8 g of the anhydrous salt in water and making up to 100 mL. 50 mL of this solution was nebulized into 900 mL of methyl alcohol using a Sono-Tek ultrasonic nozzle (Model # S/N 12096), operated under the manufacturers recommended conditions. After the salt particles had settled, the aqueous methanol was decanted. To the damp particles was added 400 mL of dry methanol; the suspension was stirred and filtered using a fine glass filter. The particles were washed with about 100 mL of dry methanol and dried over calcium chloride dessicant, which adsorbs alcohol, as well as water.

Samples of the dry particles, which consisted of crystalline spheroids of sodium pyrophosphate hexahydrate of about 3 microns in diameter, were then heated at the temperatures and times detailed in Table 1. After heating, the samples were allowed to cool to room temperature in a dessicator and 50 mg were added to a stirred beaker containing 200 mL water at room temperature (25° C.). The conductivity of this mixture was continuously monitored over the next 120 minutes to determine the solubility characteristics of the samples. The conductivity of aqueous solutions of sodium pyrophosphate is directly proportional to the concentration of salt. Thus, the conductivity (in mmho/cm) of the dissolving particles is a measure of the dissolved fraction of the solid particle.

As can be seen from the results reported in Table 1 and FIG. 1, the particle dissolution rate significantly decreases as function of increasing temperature and time of heating. As shown in Table 1, very rapid dissolution, in which complete dissolution of the particles occurs in less than 5 minutes, is evident when the particles are prepared by heating at 200° C., for the time periods indicated in Table 1. When the particles are prepared by heating at 300° C. or greater, for the time periods shown in Table 1, the particles become largely insoluble. When particles are prepared by heating at intermediate temperatures, in the range of about 250° to 275° C., phosphate particles are prepared having varying solubility (i.e., varying dissolution rates) in the range between the extremes of rapid dissolution and insolubility.

TABLE 1

Solubility of Particles Prepared from Disodium Pyrophosphate

| Temp (°C.) | Time Heated (hr) | Conductivity (μmhos/cm) of Solution at Time in Solution of: | | | | | | | | |
|---|---|---|---|---|---|---|---|---|---|---|
| | | 5 min | 10 min | 15 min | 20 min | 25 min | 30 min | 45 min | 60 min | 120 min |
| 200 | 2 | 220 | 220 | 220 | 220 | 220 | 220 | 220 | 220 | 220 |
| | 4 | 220 | 220 | 220 | 220 | 220 | 220 | 220 | 220 | 220 |
| | 7 | 223 | 223 | 223 | 223 | 223 | 223 | 223 | 223 | 223 |
| 250 | 2 | 207 | 207 | 207 | 207 | 207 | 207 | 207 | 207 | 207 |
| | 4 | 178 | 181 | 183 | 185 | 187 | 190 | 190 | 190 | 190 |
| | 6 | 167 | 174 | 178 | 179 | 180 | 180 | 181 | 181 | 181 |
| 260 | 2 | 148 | 159 | 161 | 163 | 170 | 174 | 179 | 179 | 179 |
| | 4 | 107 | 111 | 119 | 124 | 129 | 136 | 150 | 157 | 160 |

TABLE 1-continued

Solubility of Particles Prepared from Disodium Pyrophosphate

| Temp (°C.) | Time Heated (hr) | Conductivity (μmhos/cm) of Solution at Time in Solution of: | | | | | | | | |
|---|---|---|---|---|---|---|---|---|---|---|
| | | 5 min | 10 min | 15 min | 20 min | 25 min | 30 min | 45 min | 60 min | 120 min |
| | 6 | 90 | 94 | 100 | 103 | 110 | 114 | 123 | 132 | 149 |
| 275 | 2 | 69 | 72 | 74 | 77 | 80 | 82 | 83 | 84 | 93 |
| | 4 | 30 | 33 | 35 | 37 | 40 | 41 | 44 | 53 | 62 |
| | 6 | 20 | 23 | 24 | 26 | 28 | 30 | 33 | 39 | 50 |
| 300 | 3 | 15 | 16 | 19 | 20 | 21 | 23 | 26 | 32 | 43 |
| | 5 | 17 | 19 | 21 | 23 | 25 | 27 | 30 | 32 | 40 |
| | 7 | 18 | 19 | 22 | 23 | 25 | 27 | 28 | 31 | 34 |
| 400 | 2 | 4 | 5 | 5 | 6 | 7 | 8 | 8 | 10 | 11 |
| | 5 | 3 | 4 | 5 | 5 | 6 | 7 | 8 | 9 | 9 |
| | 7 | 4 | 5 | 5 | 5 | 6 | 7 | 7 | 8 | 9 |

Note: Unheated disodium pyrophosphate gave a solution conductivity of 220 μmhos/cm at <5 min following being added to water.

All solutions contained 50 mg of phosphate solid in 200 mL H$_2$O at room temperature.

FIG. 1 shows the dissolution rate of sodium phosphate particles prepared as described above, with heating at 260° C. for 1-6 hours. As shown in FIG. 1, the rate of dissolution of the particles depends on the time of heating at 260° C. Thus, by controlling the temperature and time of heating of the phosphate particle, the extent of solubility of the particle in aqueous solution can be controlled.

EXAMPLE 3

PREPARATION OF POROUS PHOSPHATE PARTICLES OF VARYING SOLUBILITY

An aqueous solution of disodium dihydrogen phosphate is introduced into a spray drying apparatus or into a high temperature aerosol decomposition (HTAD) apparatus of the type described originally by Roy et al. (1956) J. Am. Ceram. Soc. 39: 434 and as reviewed in Moser and Lennhoff (1989) Chem. Eng. Comm. 83: 241-259.

The crust-forming step and the subsequent evaporation steps may be carried out at temperatures of less than about 250° C., in order to prevent any condensation, polymerization, or other chemical changes in the phosphate shell material during formation of the particle during the spray drying or HTAD process. The overall size of the resulting particles should be no greater than about 5-10 microns. The particles should be collected in a manner that attrition and exposure to moisture is avoided.

The resultant hollow phosphate particles are then heated in a temperature controlled furnace at a temperature and for a time that will produce condensed forms of phosphate with reduced solubility, such as the forms of phosphate indicated in FIG. 1 and including the formation of polyphosphates and metaphosphates. The porous phosphate particles are usually heated in the range of about 250°-275° C., for example at about 260° C. for such a time that particles of the desired solubility are obtained. As discussed above, the extent of condensed forms of phosphate with reduced solubility in the particle is increased with increasing temperature and/or increasing time of heating.

The temperature and duration of the heating of the porous partilces is selected such that the particles obtained have the desired solubility in aqueous solution.

The porous particles so obtained after heat treatment are stored in a dry atmosphere, which may consist of an inert gas with low water solubility, until used for acoustic imaging purposes.

Alternatively, the phosphate particles may be heated during the spray drying or HTAD step at temperatures greater than about 250° C. to produce particles comprising condensed forms of phosphate and with the desired solubility.

EXAMPLE 4

PREPARATION OF SOLID CALCIUM AND SODIUM PHOSPHATE PARTICLES OF VARYING SOLUBILITY

Powdered calcium metaphosphate, Ca(PO$_3$)$_2$, (27.6 g) and 29.8 g sodium dihydrogen phosphate, NaH$_2$PO$_4$.H$_2$O, were mixed and heated in a platinum dish to 1000° C. The moderately viscous liquid was poured onto a cold steel plate to give a clear glass. This was ground up and sieved to give a particle size of about 100 microns. This composition corresponds to an intimate mixture of Ca(PO$_3$)$_2$ and NaPO$_3$ in a molar ratio of Ca:Na of 1:2.

By taking appropriate other ratios of starting ingredients there were prepared other glasses of calcium-sodium metaphophte in the molar ratios of Ca:Na of 1:4, 1:10, and 1:20.

The rate of dissolution in water was measured for the powders in water by measuring light scattering. The results below are expressed in the time in minutes required to dissolve one half of the sample with stirring:

| Composition (Ca:Na) | T½ (min) |
|---|---|
| 1:2 | very slow |
| 1:4 | 105 |
| 1:10 | 5.7 |
| 1:20 | 7.0 |

What is claimed is:

1. An ultrasound contrast agent comprising a pharmaceutically acceptable carrier and porous particles of an inorganic material containing an entrapped gas and having an average particle diameter of 0.01 to 500 microns, said inorganic material being selected from one or more of the group consisting of: monomeric or polymeric borates; monomeric or polymeric aluminas; monomeric or polymeric carbonates and bicarbonates; monomeric or polymeric silicas and silicates; monomeric or polymeric aluminosilicates; and monomeric or polymeric phosphates; and pharmaceutically acceptable organic or inorganic cationic salts thereof.

2. An ultrasound contrast agent of claim 1, wherein the inorganic material is in a crystalline form.

3. An ultrasound contrast agent of claim 1, wherein the inorganic material is in an amorphous form.

4. An ultrasound contrast agent of claim 1, wherein the inorganic material is a mixture of crystalline and amorphous forms.

5. An ultrasound contrast agent of claim 1, wherein the entrapped gas is selected from the group consisting of air, $O_2$, $N_2$, $H_2$, $CO_2$, He, Ne, Ar, $CF_4$, and $C_2F_6$.

6. An ultrasound contrast agent of claim 1, wherein the average particle diameter is 0.05 to 10 microns.

7. An ultrasound contrast agent of claim 1, wherein the porous particles have a single pore which is entirely or partially enclosed by a shell of the inorganic material.

8. An ultrasound contrast agent of claim 7, wherein the shell thickness is 1–45% of the average particle diameter.

9. An ultrasound contrast agent of claim 1, wherein the porous particles have a plurality of pores which are entirely or partially enclosed by the inorganic material.

10. An ultrasound contrast agent of claim 9, wherein the pores are interconnected.

11. An ultrasound contrast agent of claim 1, wherein the porous particles of inorganic material have a density of less than about 90% of the density of the inorganic material in a solid non-porous state.

12. An ultrasound contrast agent of claim 1, wherein the porous particles of inorganic material have a density of less than about 60% of the density of the inorganic material in a solid non-porous state.

13. An ultrasound contrast agent of claim 12, wherein the porous particles of inorganic material have a density of 0.2% to 50% of the density of the inorganic material in a solid non-porous state.

14. An ultrasound contrast agent of claim 1, wherein the porous particles of inorganic material are substantially spherical in shape.

15. An ultrasound contrast agent of claim 1, wherein the inorganic material is selected from the group consisting of $SiO_2$, aluminum oxides, aluminum hydroxides, alkali salts of aluminosilicates, and $H_3BO_3$.

16. An ultrasound contrast agent of claim 15, wherein the inorganic material is crystalline or amorphous, or a mixture of crystalline and amorphous forms.

17. An ultrasound contrast agent of claim 16, wherein the average particle diameter is 0.05 to 10 microns.

18. An ultrasound contrast agent of claim 16, wherein the porous particles have a single pore which is entirely or partially enclosed by a shell of the inorganic material.

19. An ultrasound contrast agent of claim 18, wherein the shell thickness is 1–45% of the average diameter of the particle.

20. An ultrasound contrast agent of claim 16, wherein the porous particles have a plurality of pores which are entirely or partially enclosed by the inorganic material.

21. An ultrasound contrast agent of claim 20, wherein the pores are interconnected.

22. An ultrasound contrast agent of claim 16, wherein the porous particles or inorganic material have a density of less than about 70% of the density of the inorganic material in a solid nonporous state.

23. An ultrasound contrast agent of claim 16, wherein the porous particles are substantially spherical in shape.

24. An ultrasound contrast agent of claim 16, wherein the porous particles of inorganic material are coated with an organic material.

25. An ultrasound contrast agent of claim 16, wherein the porous particles of inorganic material are coated with an organic material selected from the group consisting of ethylcellulose, hydroxypropylcellulose, methylcellulose, hydroxypropylmethylcellulose, polyvinylpyrrolidone, polyethylene glycol, albumin, gelatin, starch, collagen, dextran, modified dextrans, polylactide/polyglycolide, polyalkylcyanoacrylates, polyacrylamide, cholesterol, phosphatidylcholine, phosphatidylinositol, polysorbates, polyethlyene ethers, polyethylene esters, and polyoxyethylene/polyoxypropylene block polymers.

26. In a method of ultrasound imaging a selected tissue or organ system in a mammal, the improvement comprising introducing to the mammal an amount of an ultrasound contrast agent of claim 16, effective to alter the ultrasound echogenicity of the selected tissue or organ system.

27. An ultrasound contrast agent of claim 1, wherein the inorganic material comprises monomeric or polymeric forms, or a mixture of monomeric and polymeric forms, of phosphate.

28. An ultrasound contrast agent of claim 27, wherein the inorganic material is crystalline or amorphous, or a mixture of crystalline and amorphous forms.

29. An ultrasound contrast agent of claim 28, wherein the inorganic material comprises monomeric or polymeric forms, or a mixture of monomeric and polymeric forms, of one or more alkali cation phosphate salts.

30. An ultrasound contrast agent of claim 29, wherein the alkali cations are sodium, potassium, or calcium.

31. An ultrasound contrast agent of claim 29, wherein the porous particles of inorganic material have a density of less than about 70% of the density of the inorganic material in a solid nonporous state.

32. In a method of ultrasound imaging a selected tissue or organ system in a mammal, the improvement comprising introducing to the mammal an amount of an ultrasound contrast agent of claim 29, effective to alter the ultrasound echogenicity of the selected tissue or organ system.

33. An ultrasound contrast agent of claim 28, wherein the average particle diameter is 0.05 to 10 microns.

34. An ultrasound contrast agent of claim 28, wherein the porous particles have a single pore which is entirely or partially enclosed by a shell of the inorganic material.

35. An ultrasound contrast agent of claim 34, wherein the shell thickness is 1–45% of the average diameter of the particle.

36. An ultrasound contrast agent of claim 28, wherein the porous particles have a plurality of pores which are entirely or partially enclosed by the inorganic material.

37. An ultrasound contrast agent of claim 36, wherein the pores are interconnected.

38. An ultrasound contrast agent of claim 28, wherein the porous particles of inorganic material have a density of less than about 70% of the density of the inorganic material in a solid nonporous state.

39. An ultrasound contrast agent of claim 28, wherein the porous particles are substantially spherical in shape.

40. An ultrasound contrast agent of claim 28, wherein the porous particles of inorganic material are coated with an organic material.

41. An ultrasound contrast agent of claim 28, wherein the porous particles of inorganic material are coated with an organic material selected from the group consisting of ethylcellulose, hydroxypropylcellulose, methylcellulose, hydroxypropylmethylcellulose, polyvinylpyrrolidone, polyethylene glycol, albumin, gelatin, starch, collagen, dextran, modified dextrans, polylactide/polyglycolide, polyalkylcyanoacrylates, polyacrylamide, cholesterol, phosphatidylcholine, phosphatidylinositol, polysorbates, polyethlyene ethers, polyethylene esters, and polyoxyethylene/polyoxypropylene block polymers.

42. In a method of ultrasound imaging a selected tissue or organ system in a mammal, the improvement comprising introducing to the mammal an amount of an ultrasound contrast agent of claim 28, effective to alter the ultrasound echogenicity of the selected tissue or organ system.

43. An ultrasound contrast agent of claim 1, wherein the inorganic material comprises monomeric or polymeric forms, or a mixture of monomeric and polymeric forms, of carbonate or bicarbonate.

44. An ultrasound contrast agent of claim 43, wherein the inorganic material is crystalline or amorphous, or a mixture of crystalline and amorphous forms.

45. An ultrasound contrast agent of claim 44, wherein the inorganic material comprises monomeric or polymeric forms, or a mixture of monomeric and polymeric forms, of one or more alkali cation carbonate or bicarbonate salts.

46. An ultrasound contrast agent of claim 45, wherein the alkali cations are sodium, potassium, or calcium.

47. An ultrasound contrast agent of claim 45, wherein the porous particles of inorganic material have a density of less than about 70% of the density of the inorganic material in a solid nonporous state.

48. An ultrasound contrast agent of claim 44, wherein the average particle diameter is 0.05 to 10 microns.

49. An ultrasound contrast agent of claim 44, wherein the porous particles have a single pore which is entirely or partially enclosed by a shell of the inorganic material.

50. An ultrasound contrast agent of claim 49, wherein the shell thickness is 1–45% of the diameter of the particle.

51. An ultrasound contrast agent of claim 44, wherein the porous particles have a plurality of pores which are entirely or partially enclosed by the inorganic material.

52. An ultrasound contrast agent of claim 51, wherein the pores are interconnected.

53. An ultrasound contrast agent of claim 44, wherein the porous particles of inorganic material have a density of less than about 70% of the density of the inorganic material in a solid nonporous state.

54. An ultrasound contrast agent of claim 44, wherein the porous particles are substantially spherical in shape.

55. An ultrasound contrast agent of claim 44, wherein the porous particles of inorganic material are coated with an organic material.

56. An ultrasound contrast agent of claim 44, wherein the porous particles of inorganic material are coated with an organic material selected from the group consisting of ethylcellulose, hydroxypropylcellulose, methylcellulose, hydroxypropylmethylcellulose, polyvinylpyrrolidone, polyethylene glycol, albumin, gelatin, starch, collagen, dextran, modified dextrans, polylactide/polyglycolide, polyalkylcyanoacrylates, polyacrylamide, cholesterol, phosphatidylcholine, phosphatidylinositol, polysorbates, polyethlyene ethers, polyethylene esters, and polyoxyethylene/polyoxypropylene block polymers.

57. In a method of ultrasound imaging a selected tissue or organ system in a mammal, the improvement comprising introducing to the mammal an amount of an ultrasound contrast agent of claim 44, effective to alter the ultrasound echogenicity of the selected tissue or organ system.

58. An ultrasound contrast agent of claim 1, wherein the porous particles of inorganic material are coated with an organic material.

59. An ultrasound contrast agent of claim 1, wherein the porous particles of inorganic material are coated with an organic material selected from the group consisting of ethylcellulose, hydroxypropylcellulose, methylcellulose, hydroxypropylmethylcellulose, polyvinylpyrrolidone, polyethylene glycol, albumin, gelatin, starch, collagen, dextran, modified dextrans, polylactide/polyglycolide, polyalkylcyanoacrylates, polyacrylamide, cholesterol, phosphatidylcholine, phosphatidylinositol, polysorbates, polyethlyene ethers, polyethylene esters, and polyoxyethylene/polyoxypropylene block polymers.

60. In a method of ultrasound imaging a selected tissue or organ system in a mammal, the improvement comprising introducing to the mammal an amount of an ultrasound contrast agent of claim 1, effective to alter the ultrasound echogenicity of the selected tissue or organ system.

* * * * *